(12) United States Patent
Luo et al.

(10) Patent No.: US 8,964,185 B1
(45) Date of Patent: Feb. 24, 2015

(54) GAS DETECTION SYSTEM USING A FIBER LASER WITH DOUBLE-WAVELENGTH COMBINATION HAVING REFERENCE-CAVITY COMPENSATION FUNCTION

(71) Applicant: Beijing Information Science & Technology University, Beijing (CN)

(72) Inventors: Fei Luo, Winchester, MA (US); Lianqing Zhu, Beijing (CN); Mingli Dong, Beijing (CN); Wei He, Beijing (CN); Yinmin Zhang, Beijing (CN)

(73) Assignee: Beijing Information Science & Technology University, Beijing (CN)

( * ) Notice: Subject to any disclaimer, the term of this patent is extended or adjusted under 35 U.S.C. 154(b) by 0 days.

(21) Appl. No.: 14/503,939

(22) Filed: Oct. 1, 2014

(30) Foreign Application Priority Data

Oct. 14, 2013 (CN) .......................... 2013 1 0479339

(51) Int. Cl.
*G01N 21/00* (2006.01)
*G01N 21/61* (2006.01)
*G01N 33/00* (2006.01)

(52) U.S. Cl.
CPC ............ *G01N 21/61* (2013.01); *G01N 33/0036* (2013.01)
USPC ......................................... 356/436; 356/437

(58) Field of Classification Search
CPC .............. G01N 21/39; G01N 21/3504; G01N 21/0332; G01N 2021/399; G01N 2021/1793; G01N 21/0303; G01N 21/031; G01N 21/171; G01N 21/3554; G01N 21/538; G01N 2291/011; G01N 2291/022; G01N 2291/024
See application file for complete search history.

(56) References Cited

U.S. PATENT DOCUMENTS

| | | | |
|---|---|---|---|
| 7,136,219 B2 | 11/2006 | Shimizu et al. | |
| 2007/0246653 A1* | 10/2007 | Zhou | 250/339.1 |
| 2008/0204698 A1* | 8/2008 | Rohner et al. | 356/4.01 |
| 2009/0303486 A1* | 12/2009 | Magari et al. | 356/437 |
| 2011/0122906 A1* | 5/2011 | Seeley et al. | 372/38.07 |

FOREIGN PATENT DOCUMENTS

| | | |
|---|---|---|
| CN | 101251481 A | 8/2008 |
| CN | 101251482 A | 8/2008 |

(Continued)

OTHER PUBLICATIONS

Qi Jie et al., Research on fiber gas sensor system based on average filtering algorithm, Laser & Infrared, 2012, vol. 42 No. 5.

(Continued)

*Primary Examiner* — Michael P Stafira
(74) *Attorney, Agent, or Firm* — Tim Tingkang Xia, Esq.; Morris, Manning & Martin, LLP

(57) ABSTRACT

A fiber laser gas detection system with a double wavelength combination using reference cavity compensation is provided. The system comprises an optical fiber laser respectively emitting beams having a first and second wavelengths, which consists of a laser diode pump source, a first wavelength division multiplexer, an active optical fiber, a first fiber bragg grating and a second fiber bragg grating connected successively; an optical isolator; a coupler for dividing the beams according to power ratio, the divided beams is introduced into a reference gas chamber and a detecting gas chamber respectively; a second wavelength division multiplexer connecting the reference room and a third wavelength division multiplexer connecting the detecting gas chamber; a first, a second, a third and a fourth photoelectric detector; a feedback control unit, receiving the first to fourth light intensity signals and adjusting the fiber laser using the comparison results as a feedback signal.

10 Claims, 4 Drawing Sheets

(56) References Cited

FOREIGN PATENT DOCUMENTS

| CN | 102305771 A | 1/2012 |
| CN | 102323527 A | 1/2012 |
| CN | 202260115 U | 5/2012 |
| CN | 103196852 A | 7/2013 |

OTHER PUBLICATIONS

Yu Kuang Lu et al., Research Progress on Multi-point Gas Sensor Network, Semiconductor Optoelectronics, 2010, vol. 31 No. 1.
Patent Search & Consulting Center of State Intellectual Property Office, "Search Report", Dec. 18, 2013.

* cited by examiner

GAS DETECTION SYSTEM USING A FIBER LASER WITH DOUBLE-WAVELENGTH COMBINATION HAVING REFERENCE-CAVITY COMPENSATION FUNCTION

CROSS-REFERENCE TO RELATED APPLICATIONS

This non-provisional application claims priority under 35 U.S.C. §119(a) on Patent Application No. 201310479339X filed in P.R. China on Oct. 14, 2013, the entire contents of which are hereby incorporated by reference.

TECHNICAL FIELD

The present invention relates to a fiber laser, particularly relates to a gas detection system and method for the gas concentration measurement implemented by a fiber laser with a double-wavelength combination using reference cavity compensation.

BACKGROUND OF THE INVENTION

Every kind of gas molecules has its own characteristic spectral line. So supposed that the emission spectrum of light source is overlapped with the absorption spectrum of gas, it can be designed to make the light emitted by a narrow-band light source or a laser light source pass through the gas to be detected, and then determine the concentration of the gas by measuring the intensity of the transmission light. Generally the absorption spectral linewidth of the ordinary light source is relatively wide, while the absorption spectral linewidth of some gas is very narrow. Thus the change of the light power after passing through the gas chamber is not obvious, leading to the measuring sensitivity is not very high. In contrast, the spectral lines outputted by the laser light source is relatively narrow, which is suitable for measuring a variety of gas.

Laser plays an important role in modern spectroscopy, due to its high monochromaticity (narrow spectral line), high brightness, high directivity and other unique advantages. A new laser spectroscopy develops, with an important practical application value in various research fields such as modern agriculture and environmental science, biology and medical science, physics, chemistry and materials science and astrophysics, and in industrial process monitoring.

Laser used for gas detection has an important application value in environmental detection and analysis, as well as a variety of industrial process control, etc. Each gas molecules has its characteristic spectral lines, so certain gases can be detected by using the characteristics of the laser having narrow linewidth. One of common gas detection methods by laser is to adjust or set the wavelength emitted from the laser to be consistent with the characteristic absorption spectrum line of the gas to be detected, to transmit the laser through the gas chamber, and thus to determine the concentration of the gas by measuring the attenuation of the laser after transmitting through the gas cavity. This detecting method is simple in both the principle and the structure. However, generally the ordinary light source has a wide spectral linewidth, and some of the gases have very narrow absorption lines, so the optical power does not change obviously when passing through the gas chamber, which lowers and limits measuring sensitivity. Especially, it is more difficult for detecting tiny gas concentration.

The conventional differential absorption method is achieved based on two beams in a common optical path passing through the same gas cavity to be detected. The output beam wavelength of one beam is consistent with the characteristics absorption lines of the gas to be detected. And the output beam wavelength of the adjacent beam is selected near the absorption lines of the gas to be detected, but not exactly the same with its absorption lines, to be used as a reference light in order to eliminate the instability of light intensity in the light path. However, this detection method does not eliminate the detection error caused by the instability of the wavelength of light, which can not be ignored in the practical detection. Therefore, in the prior art, the differential absorption method is improved. Commonly, the laser current and temperature is stabilized to realize a stable wavelength outputted from the laser. However such a regulation method is passive, do not strictly eliminate fluctuations of the laser, thus such an improvement do not obtain good effects.

Fiber laser is a new type laser developed rapidly in recent years. Fiber laser uses a fiber optic waveguide as a gain medium and an optical fiber grating as a feedback mirror to form an integrated optical fiber resonator, thus providing advantages such as compact structure, narrow laser linewidth, high beam quality, and a laser system with high reliability, good stability and maintenance-free, which makes a huge impact on the laser industry. Development of modern spectral composition detection and analysis system based on fiber laser will not only has great significance to the development of laser spectroscopy, but also make the fiber laser spectral analysis system more portable to be used expediently. Therefore, it is a technical problem to be solved in this field as how to apply the fiber laser in the field of gas concentration detection taking various advantages of the fiber laser, such as its compact structure, narrow linewidth of the laser output. There is a need for a gas concentration measurement method and system which not only taking advantages of fiber laser but also obtaining high sensitivity and high precision of gas detection.

SUMMARY OF THE INVENTION

The present invention provides a fiber laser gas detection system with a double wavelength combination having a reference-cavity compensation function, said system comprising: an optical fiber laser emitting the beams having the first wavelength and the second wavelength respectively, which consists of a laser diode pump source, a first wavelength division multiplexer, an active optical fiber and a first fiber bragg grating and a second fiber bragg grating connected successively, said first wavelength is different from said second wavelength, said first wavelength is the same as the characteristic absorption lines of the gas to be detected; an optical isolator coupling connected with said first wavelength division multiplexer, said optical isolator is used to prevent reverse light from transmitting in said active optical fiber; a coupler connected with said optical isolator for dividing the laser light after being synthesized by said first wavelength division multiplexer into a first and second outputs according a certain power proportion; a reference gas chamber, which is filled with the reference gas of the a known concentration and of the same composition as that of the gas to be detected, and receives the first output beam from said coupler to pass through the reference gas; a detection gas chamber, which is filled with the gas to be detected, and receives the second output beam from said coupler to pass through the gas to be detected; a second wavelength division multiplexer connected with said reference gas chamber, for dividing the beam passing through the reference gas chamber into beams having said first wavelength and said second wavelength; a third wavelength division multiplexer connected with said detecting gas chamber, for dividing the beam passing through the detecting gas chamber into beams having said first wavelength and said second wavelength; a first photodetector connected to said second wavelength division multiplexer for receiving the divided beam having the first wavelength to generate a first light intensity signal; a second photodetector connected to said second wavelength division multiplexer for receiving the divided beam having the second wavelength to generate a second light intensity signal; a third photodetector connected to said third wavelength division multiplexer for receiving the divided beam having the first wavelength to generate a third light intensity signal; a fourth photodetector connected to said third wavelength division multiplexer for receiving the divided beam having the second wavelength to generate a fourth light intensity signal; a feedback control unit for receiving and comparing said first, second, third and fourth light intensity signals, and converting the comparison result into a feedback signal to adjust said pump source and said first fiber bragg grating.

Preferably, wherein said coupler emits the first and second output according to the power ratio of 1:1.

Preferably, wherein the feedback control method of the feedback control unit comprising the steps of: a) determining whether the output of the fiber laser is stable, if it is not stable, sending out a first feedback control signal to adjust the power output of the pump source until it is stable; b) determining whether the wavelength range of the signal mode having the first wavelength covers the characteristics spectral lines of the gas to be detected, if it does not cover, then sending out a second feedback control signal to adjust the first fiber bragg grating until it covers; c) determining whether the second light intensity signal is different from the fourth light intensity signal, if there is any difference, a signal indicating the difference is used for compensating the first light intensity signal and the third light intensity signal; and d) comparing the signal intensities of the first and third light intensity signals to obtain the result of comparing the concentrations of the gas to be detected and the reference gas.

Preferably, said step b) is achieved by comparing if the signal intensity values of said first or third light intensity is substantially smaller than that of the second or the fourth light intensity signal to determine whether it covers.

Preferably, it further comprises a laser control unit attached to the first fiber bragg grating, and the deformation of the laser control unit is controlled by said second feedback control signal so as to change the laser resonator cavity length.

Preferably, the laser control unit is made of PZT piezoelectric ceramic or TE temperature control unit.

Preferably, it further comprises a spherical lens for respectively coupling said beams into the reference gas chamber and the detection gas chamber so as to emit therefrom.

Preferably, said second wavelength is near the wavelength of the absorption line of the gas to be detected with a distance away therefrom.

Preferably, the active fiber is an ytterbium-doped fiber, or erbium-doped fiber or erbium ytterbium co-doped fiber.

According to the other hand of the present invention, it provides a fiber laser gas detection system with a double wavelength combination having a reference-cavity compensation function, said system comprising: an optical fiber laser emitting the beam having a first wavelength, which consists of a laser diode pump source, a first wavelength division multiplexer, an active optical fiber and a fiber bragg grating connected successively; a laser light source emitting the beam having a second wavelength which is different from the first wavelength, said first wavelength is the same as the characteristic absorption lines of the gas to be detected; a first optical isolator coupling connected with said first wavelength division multiplexer, said optical isolator is used to prevent reverse light from transmitting in said active optical fiber; a second optical isolator coupling connected with said laser light source, said optical isolator is used to prevent reverse light from transmitting in said active optical fiber; a second wavelength division multiplexer connected with said first and second optical fiber, for synthesizing the beams having the first and the second wavelength into one beam to output; a coupler connected with said second wavelength division multiplexer for dividing the laser light after being synthesized by said second wavelength division multiplexer into a first and second outputs according a certain power proportion; a reference gas chamber, which is filled with the reference gas of a known concentration and of the same composition as that of the gas to be detected, and receives the first output beam from said coupler to pass through the reference gas; a detection gas chamber, which is filled with the gas to be detected, and receives the second output beam from said coupler to pass through the gas to be detected; a third wavelength division multiplexer connected with said reference gas chamber, for dividing the beam passing through the reference gas chamber according to said first wavelength and said second wavelength; a fourth wavelength division multiplexer connected with said detecting gas chamber, for dividing the beam passing through the detecting gas chamber according to said first wavelength and said second wavelength; a first photodetector connected to said third wavelength division multiplexer, for receiving the divided beam having the first wavelength to generate a first light intensity signal; a second photodetector connected to said third wavelength division multiplexer, for receiving the divided beam having the second wavelength to generate a second light intensity signal; a third photodetector connected to said fourth wavelength division multiplexer, for receiving the divided beam having the first wavelength to generate a third light intensity signal; a fourth photodetector connected to said fourth wavelength division multiplexer, for receiving the divided beam having the second wavelength to generate a fourth light intensity signal; a feedback control unit for receiving and comparing said first, second, third and fourth light intensity signals, and converting the comparison result into a feedback signal to adjust said pump source, said fiber bragg grating and said laser light source.

The gas detection system according to the present invention can take advantages of the unique superiority of the fiber laser, i.e., the compact structure and narrow linewidth of the laser output, and achieve a gas detection method with high sensitive and high precision by feedback controlling, eliminating the detecting error of the drift of the detecting environment. The method and system are not limited to apply to high sensitivity detection of gas content, but also easily apply to the detection with high sensitivity and material analysis of other materials.

It should be understood that the foregoing general description and the following detailed description are merely exemplary explanation, and shall not be construed as limiting the contents as claimed by the invention.

BRIEF DESCRIPTION OF DRAWINGS

Further objects, functions, and advantages of the present invention will be explained in details by embodiments of the present invention with reference to the accompanying drawings.

DETAILED DESCRIPTION OF THE INVENTION

Figure 1:
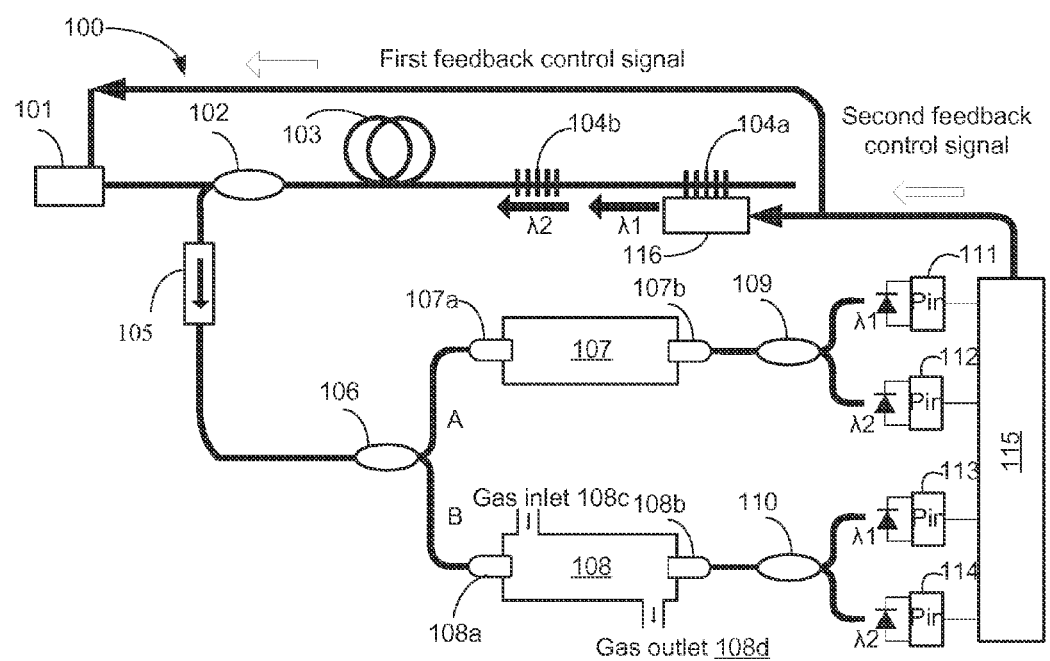
FIG. 1 schematically shows a gas detection system using a fiber laser of a double wavelength combination using reference cavity compensation according to an embodiment of the present invention.

Hereinafter, embodiments of the present invention will be explained in details with reference to drawings. In the accompanying drawings, like reference numerals designate the same or similar parts, or the same or similar procedures.

With reference to the exemplary embodiments, the purpose and function of the present invention and method to achieve these purpose and function will be explained. However, the present invention is not limited to the disclosed exemplary embodiments, and can be implemented with different forms. The description is merely to help those skilled in the art to comprehensively understand the specific details of the invention.

The present invention will be described in detail with reference to the schematic Figures. For the purpose of explanation, when describing the invention in details, the sectional figures representing the device structure will be partial enlarged not in general proportion, and the schematic Figures are only exemplary and not intended to limit the scope claimed by the invention. Moreover, it should comprise three space dimensions of length, width and depth in the actual production.

The present invention provides a gas detection system that has the function of active correction and active frequency stabilization based on the distributed feedback (DFB) fiber laser, which is characterized in using a semiconductor laser as a pump source of the DFB fiber laser, emitting a laser of specific wavelength, coupling the laser into a coupler by the wavelength division multiplexer (WDM), dividing the input light into two beams by the coupler, emitting the two beams into the reference gas chamber and the detecting gas chamber respectively for differential comparison. Transmission beams are detected by the photoelectric detectors, and the signals received are analyzed and processed to achieve the feedback control of the DFB fiber laser.

In the present invention, a standard cavity is introduced which is filled with the same gas as that to be detected of a known concentration and is completely sealed. The laser outputted from the optical fiber laser is designed to couple and pass through the detection gas cavity and the standard cavity respectively. The signal outputted from the standard cavity on the one hand can be used for active correction by the comparison with the output of the detection gas cavity, on the other hand, it can be used for the active frequency stabilization of the wavelength of the detection light. The system eliminates the interferences to measurement caused by the intensity fluctuation and the environmental interferences, so as to implement accurate measurement of the gas to be detected. The gas detection system according to the present invention is particularly suitable for threshold detection of tiny gas concentration in certain situation for gas safety alarm.

With full use of the unique advantages of the fiber laser such as the compact structure and emitting laser beam with a plurality of narrow linewidths, the present invention adopts the distributed feedback (DFB) semiconductor laser, which is a kind of single longitudinal mode semiconductor laser (Laser Diode) with excellent frequency selective characteristics. DFB LD light source can operate in a single longitudinal mode with the output laser having a narrow spectral linewidth which is up to tens of kilohertz, and can make the operating laser wavelength precisely aligning with the characteristic absorption peaks of the gas being measured by regulating the temperature or the drive current of the laser, to improve the measurement precision highly. The gas detection method and system with high sensitivity and precision is implemented in the present invention, the method and system are not limited to the detection of gas content with high sensitivity, also be easily extended to the detection with high sensitivity and the material analysis of other materials.

Generally the spectral absorption detection satisfies Bill-Lambert's law as follows:

$$I(\lambda)=I_0(\lambda)\exp[-\alpha(\lambda)CL] \tag{1}$$

Wherein, I is the intensity of the light transmitted through the medium to be detected, $I_0$ is the intensity of the light inputted into the medium to be detected, $\alpha$ is the molar absorption coefficient, C is the concentration of the medium to be detected, L is the length of the absorption path for the medium to be detected. Generally it is known that the incident light intensity is denoted as $I_0$, the absorption coefficient for the gas to be detected in its characteristic spectral lines is denoted as $\alpha$, the length of the gas sampling cavity for measuring the gas to be detected is denoted as L, the concentration of the gas C can be measured by measuring the optical signal attenuation of the laser having the specific wavelength after it comes through the gas absorption chamber.

Generally, the light can be interfered by various factors in the light transmission path, such as the vibration, the unstable beam wavelength outputted from the laser, etc. All factors will seriously interfere with the actual measurement result. Considering the influence of these factors, the principle of spectral absorption detection can be revised to:

$$I(\lambda)=I_0(\lambda)K(\lambda)\exp[-\alpha(\lambda)CL+\beta(\lambda)] \tag{2}$$

Wherein, $K(\lambda)$ is the fluctuation of the light source and the light transmission path, $\beta(\lambda)$ is the measurement uncertainty caused by the laser spectrum fluctuation, thus the key problem in measuring the gas concentration by the conventional absorption method is how to effectively reduce the influence on measurement by $K(\lambda)$ and $\beta(\lambda)$.

According to the system of the present invention, the center wavelength of the laser and the gas absorption peak are aligned, the concentration of the gas can be detected by measuring the loss of light while it passing through the gas. Because of the gas absorption peak is very narrow, the drift of the light wavelength with the influence of environment (temperature, drive current, etc.) will cause the center wavelength of the light deviates from the center wavelength of the gas absorption peak, the absorption coefficient of the gas to be detected itself may changes with temperature, etc, and thus lead to unstable measurement. So it needs to make the wavelength of the light source precisely keep stable in the center wavelength of the gas absorption peak. According to the present invention, the stability of the wavelength can be implemented by the method of stabilizing the frequency outputted by the light source and introducing an additional reference gas chamber, as described below. FIG. 1 is a diagram of the system structure according to the present invention.

FIG. 1 shows a gas detection system of a fiber laser with double wavelength combination using reference cavity compensation according to the present invention. The gas detection system 100 according to the present invention comprises a DFB fiber laser which outputs two different laser wavelengths and is consisted of a laser diode pump source 101, a first wavelength division multiplexer 102, an active optical fiber 103, a first fiber bragg grating 104a and a second bragg grating 104b connected successively; a optical isolator 105 coupled with the first wavelength division multiplexer 102; a optical isolator coupler 106 connected with the optical isolator 105, the optical isolator coupler 106 is connected with a reference gas chamber 107 and a detecting gas chamber 108, while a second wavelength division multiplexer 109 and a third wavelength division multiplexer are connected with the other end of the reference gas chamber 107 and the detecting gas chamber 108. The light outputted from the second wavelength division multiplexer 109 is inputted into a first photoelectric detector 111 and a second photoelectric detector 112, the light outputted from the second wavelength division multiplexer 110 is inputted into a third photoelectric detector 113 and a forth photoelectric detector 114, and the light signals are converted into electrical signals so as to detect the intensity of the light signal after passing through each gas chamber respectively. The output ends of the first photoelectric detector 111, the second photoelectric detector 112, the third photoelectric detector 113, and the fourth photoelectric detector 114 are connected to the feedback control unit 115, so as to implement feedback control to the pump sources 101 and the laser control unit 116, and obtain a detecting result of the gas concentration by comparison calculation.

The pump source 101 emits a pump light which is coupled into the active optical fiber 103 by the wavelength division multiplexer (WDM) 102, and the active optical fiber 103 combines with the first fiber bragg grating 104a and the second fiber bragg grating 104b directly written on the active optical fiber 103 to form a resonant cavity, which constitute the DFB fiber laser which output two different wavelength laser. Preferably, the first wavelength division multiplexer 102 is 1×2 wavelength division multiplexer, allowing two lights of different wavelengths transmit in the same optical fiber.

The parameters of the first Bragg fiber grating 104a and the second Bragg fiber grating 104b can be adjusted to obtain a laser output having a specified wavelength. Fiber laser requires an output in single longitudinal mode. The narrower the output linewidth is, the better the linewidth of the output of the laser is coincident with the absorption characteristic spectral lines of the gas, and the higher the measuring precision of gas concentration will be.

The resonator cavity consisted by the first fiber Bragg grating 104a is adjusted to emit the first beam of the first wavelength $\lambda_1$ as the detecting beam, the resonator cavity consisted by the second fiber Bragg grating 104b is adjusted to emit the second beam of the second wavelength $\lambda_2$ as the reference beam. The first wavelength $\lambda_1$ is different from the second wavelength $\lambda_2$. The first wavelength of the detecting light beam is the same as the characteristics absorption lines of gas to be detected, and the second wavelength of the reference beam is near the absorption lines of the gas to be detected, but with a distance away from its absorption lines. According to a embodiment of the present invention, when the gas to be detected is methane gas, the characteristic absorption lines is 1.3 μm, at this time the first wavelength of the first beam is 1.3 μm, and the second wavelength of the second beam is 1.5 μm, and with an interval of 0.2 μm different from the first wavelength.

The first light beam of the first wavelength $\lambda_1$ and the second beam of the second wavelength $\lambda_2$ output together to the first wavelength division multiplexer 102, thus the light signal of the first light beam and the second light beam carrying the information but having different wavelengths are combined into a single light beam to emit. The operating wavelength of the first wavelength division multiplexer 102 is selected to cover the same wavelength range as those of the first light beam and the second light beam. According to the above embodiments, when the gas to be detected is methane gas, the operating wavelength of the wavelength division multiplexer 102 may be near 1310/1550 nm. Preferably, the first wavelength division multiplexer 102 is 1×2 wavelength division multiplexer, allowing two lights of different wavelengths transmit in the same optical fiber.

The active optical fiber 103 may have a shorter length (for example in cm orders of magnitude), preferably it is doped with rare earth elements and has a high doping concentration (such as erbium ytterbium codoping, peak absorption in 40+10 db/m@1535 nm), in order to reduce the threshold of the pump system. The fiber Bragg grating 104 has high reflectivity (the reflectance can be more than 90% for a specific wavelengths) to reduce the number of longitudinal mode of the output laser, and its center wavelength of reflection determines the center wavelength of the output beam. Laser diode pump source 101 is determined according to the absorption spectral line of active optical fiber 103 doped with rare earth elements. The parameters of the wavelength division multiplexer 102 and the fiber Bragg grating 104 according to the present invention should be selected to match with the pump wavelength, the laser output beam wavelength, and the parameters of the active optical fiber, the specific parameters are shown in table 1.

TABLE 1 the parameters of the short cavity fiber laser

| Doping element | Peak absorption | Cutoff wavelength | Cladding core diameter | Output laser wavelength | WDM wavelength | FLM wavelength |
|---|---|---|---|---|---|---|
| erbium (ER) | 30 dB/m@1530 nm | 800-980 nm | Single mode 125 μm | 1530 nm-1560 nm | 976/1550 nm | 1550 nm |
| ytterbium (Yb) | 80 db/m@1530 nm 280 ± 50 dB/m@920 nm 0.6 ± 0.2 dB/m@920 nm 1.8 ± 0.4 dB/m@920 nm | 1010 ± 70 nm | | 1060 nm-1090 nm | 915/1064 nm | 1064 nm |

TABLE 1-continued the parameters of the short cavity fiber laser

| Doping element | Peak absorption | Cutoff wavelength | Cladding core diameter | Output laser wavelength | WDM wavelength | FLM wavelength |
|---|---|---|---|---|---|---|
| Erbium ytterbium codoping | 0.75 ± 0.15 dB/m@915 nm<br>40 ± 10 dB/m@1535 nm | 1440 ± 80 nm | | 1530 nm-1560 nm | 976/1550 nm | 1550 nm |

According to the present invention, the core diameter of the fiber is determined by the active optical fiber used in the system, the core diameter of the cladding preferably is 125 microns, the core diameter of the optical fiber may be 4 microns, 8 microns or 10 microns, preferably 10/125 microns. The core diameters of the FLM, WDM, LD pigtail fiber should be chosen according to the selected core diameter. The pump wavelength of the Erbium-doped fiber used in this system should be 980 nm and 1480 nm, the pump wavelength of the ytterbium doped fiber should be 976 nm and 915 nm, and the pump wavelength of the erbium ytterbium doped fiber should be 976 nm. The parameters of the FLM, WDM should be determined according to the parameters of the wavelength and the core diameter. The laser wavelength being outputted finally is determined by the wavelength of the reflection of the fiber Bragg grating with a specific gain range of the active optical fiber (such as 1530-1560 nm). The typical output beam wavelength of the ytterbium doped fiber is 1535 nm, the typical output beam wavelength of the erbium-doped fiber is 1064 nm, and the typical output beam wavelength of erbium ytterbium doped fiber is 1550 nm.

For example, if in this embodiment, an erbium-doped fiber with a core diameter of 10/125 microns is used as the gain medium, LD pigtail fiber, WDM and FLM should be selected to have the core diameters of the same type. The output beam wavelength of LD is 976 nm, the operating wavelength of WDM is 976/1550 nm, the operating wavelength of FLM is 1550 nm, the range of FBG is 1530 nm to 1560 nm, a laser output can obtained within this range. If in this embodiment, an ytterbium-doped fiber with a core diameter of 10/125 microns is used as the gain medium, LD fiber, WDM and FLM should be selected to have the core diameter of the same type. LD has a 915 nm single mode output, the operating wavelength of WDM is 915/1064 nm, the operating wavelength of FLM is 1064 nm, FBG is selected near 1064 nm, a laser output can be obtained in the range. The DFB fiber laser is formed by the fiber Bragg grating 104 directly written on the active fiber 103, while the wavelength of the laser output is kept to be the same as that of the characteristics lines of the gas absorption.

The laser outputted from the fiber laser structured according to the present invention, including the first light beam of the first wavelength and the second light beam of the second wavelength, is coupled by the first wavelength division multiplexer 102 into the optical isolator 105. The optical isolator 105 is used to prevent the reverse optical transmission in the optical fiber from affecting the output light of the gas detection system 100. The operating wavelength and the isolation degree of the optical isolator 105 are chosen based on the parameters of the first and the second emission wavelength. According to a preferable embodiment of the present invention, the operating wavelength of the optical isolator 105 is 1550 nm, the isolation degree of 40 dB.

The laser after being isolated by optical isolator 105 pass through the coupler 106 with a pigtail fiber of 1×2, and is divided according to a certain power allocation ratio into two beams of light, i.e., a reference beam and a detecting beam, to output separately into the detecting gas chamber 107 and the reference gas chamber 108 subsequently connected therewith. According to a preferred embodiment of the present invention, preferably, the coupler 106 is a broadband coupler, its bandwidth should be covered a range from the first wavelength of the first light beam to the second wavelength of the second light beam. For example, in the embodiments of the above, when the first wavelength of the first light beam is 1.3 μm and the second wavelength of the second light beam is 1.5 μm, the bandwidth of the broadband coupler 104 covers a range preferably from 1.3 μm to 1.5 μm. More preferably, the coupler 106 is a broadband coupler of which the tail fiber is 1×2, its spectral ratio can be chosen as needed. According to an embodiment of the present invention, as it is required that the beams passing through the reference gas chamber 107 and the detect chamber 108 are consistent with each other, the light power of the beams passing through the two air chamber are consistent with each other. According to the present invention, preferably the allocation proportion of the power of the output laser is halved, namely the ratio of the power of the reference beam: detecting beam (i.e., beams A and B respectively, shown in the Figure) is: 1:1.

Then, after light division, two beams of light A and B are coupled into the reference gas chamber 107 and the detecting gas chamber 108 by the spherical lens 107a and 108a respectively, and then coupled to emit outwards from a spherical lens 107b and 108b. The gas inputted into the reference gas chamber 107 is of the same composition as that of the gas to be detected, and of a known concentration, and the reference gas chamber 107 is completely sealed when measuring. The reference gas chamber 107 is mainly used for wavelength correction. The wavelength drift may occur in the detecting gas chamber of the actual measurement, due to the drift of the light source wavelength, the loss change of the transmission path (e.g., sometimes up to several kilometers), the drift of the optical element in the air chamber etc. The detecting gas chamber 108 is used to let the gas to be detected pass, and the detecting gas chamber 108 includes a gas inlet 108c to introduce the gas to be detected before measuring and a gas outlet 108d to export the gas. In the measurement process, the gas inlet 108c and gas outlet 108d are closed to achieve a static measurement system.

The beam outputted through the reference gas chamber 107 is divided by the second wavelength division multiplexer (WDM) 109, the beam outputted through the reference gas chamber 108 is divided by the third wavelength division multiplexer (WDM) 110. The second wavelength division multiplexer 109 and the third wavelength division multiplexer 110 are used to beam split and output the light signals of the light beams carrying different wavelengths information according to the different wavelengths. The operating wavelengths of the second wavelength division multiplex 109 and the third wavelength division multiplex 110 are selected to cover the same wavelength range as those of the first beam and the second beam, thereby the light beam containing the first wavelength and the second wavelength is divided into two beams of light signal having the first wavelength and the second wavelength respectively. According to an embodiment of the above, when the gas to be detected is methane gas, the operating wavelengths of the second wavelength division multiplexer 109 and the third wavelength division multiplexer 110 can be near 1310/1550 nm. Preferably, the second wavelength division multiplexer 109 and the third wavelength division multiplexer 110 are 1×2 wavelength division multiplexers, allowing two lights of different wavelengths transmit in the same optical fiber.

A first photoelectric detector 111, a second photoelectric detector 112, a third photoelectric detector 113, and a fourth photoelectric detector 114 are used for detecting the intensity signals of the output light beam, and the light intensity signals are converted into electrical signal for comparison and processing. Wherein, the first photoelectric detector 111 is used to detect the intensity of the output signal of the first wavelength $\lambda_1$ which pass through the reference gas chamber 107 and is divided by the second wavelength division multiplexer 109, as a detecting wavelength signal of the reference gas chamber, that is the first light intensity signal; the second photoelectric detector 112 is used to detect the intensity of the output signal of the second wavelength $\lambda_2$ which pass through the reference gas chamber 107 and is divided by the second wavelength division multiplexer 109, as a reference wavelength signal of the reference gas chamber, that is the second light intensity signal; the third photoelectric detector 113 is used to detect the intensity of the output signal of the first wavelength $\lambda_1$ which pass through the reference gas chamber 108 and is divided by the third wavelength division multiplexer 110, as a detecting wavelength signal of the detecting gas chamber, that is the third light intensity signal; the fourth photoelectric detector 114 is used to detect the intensity of the output signal of the second wavelength $\lambda_2$ which pass through the reference gas chamber 108, and is divided by the third wavelength division multiplexer 110, as a reference wavelength signal of the detecting gas chamber, that is the fourth light intensity signal. The first light intensity signal and the third light intensity signal are regarded as the signals overlapping with the characteristics absorption lines of the gas to be detected to indicate the concentration of the gas to be detected, the second light intensity signal and the fourth light intensity signal are regarded as the reference signal not absorbed by the gas to be detected to indicate the measurement environment difference of the reference gas chamber and the detecting gas chamber. If the reference wavelength deviates, this deviation can be considered in the calculation of the wavelength measurement for compensation, and can also be used to adjust the output wavelength of the laser as the light source, thereby eliminate the measurement error due to the interference of the air chamber environment.

The intensity of the output light beam can be measured by a power meter or spectrometer. Four light intensity signals are inputted into the feedback control unit 115 for subsequent control operations. Preferably, the photoelectric detector may be made of a photoelectric diode, the operating wavelength range of the photoelectric detector should cover the wavelength range of the output beam of the fiber laser. According to a preferably embodiment of the invention, the operating wavelength of the photoelectric detector is 800-1700 nm, its bandwidth is 1.2 GHz, and its rise time is less than 1.0 ns.

The feedback control unit 115 is used to receive the light intensity signals outputted from the first, second, third and fourth photodetectors 111, 112, 113 and 114, and then the light intensity signals are compared and calculated to output the feedback control signal to the pump source 101 and the laser control unit 116, to implement feedback control. The feedback control unit 115 can be implemented by a single chip microcomputer, integrated circuits, an application specific integrated circuit, or a computer, its control method will be described in details below.

Preferably, the laser control unit 116 can be made of materials such as PZT piezoelectric ceramic or TE temperature control unit etc., that can convert electrical signals into physical deformation, so as to change the cavity length of the laser resonator cavity by material deformation controlled under the feedback signal outputted from the feedback control unit 115 to precisely control the beam wavelength outputted from the laser. According to an embodiment of the present invention, the laser control unit 113 can be made by a sheet or plate attached on the fiber Bragg grating 104a. When the feedback control unit 115 issues a control signal, the material physical properties of the laser control unit 116 can be changed to change the cavity length of the laser cavity. For example, when the laser control unit 113 is made of piezoelectric ceramic, the feedback control signal makes the laser control unit 115 deform, thus the fiber bragg grating 104a attached thereto deforms, the length of the laser cavity is changed, the wavelength of the output laser is changed, so that the output beam wavelength drifts.

Figure 2:
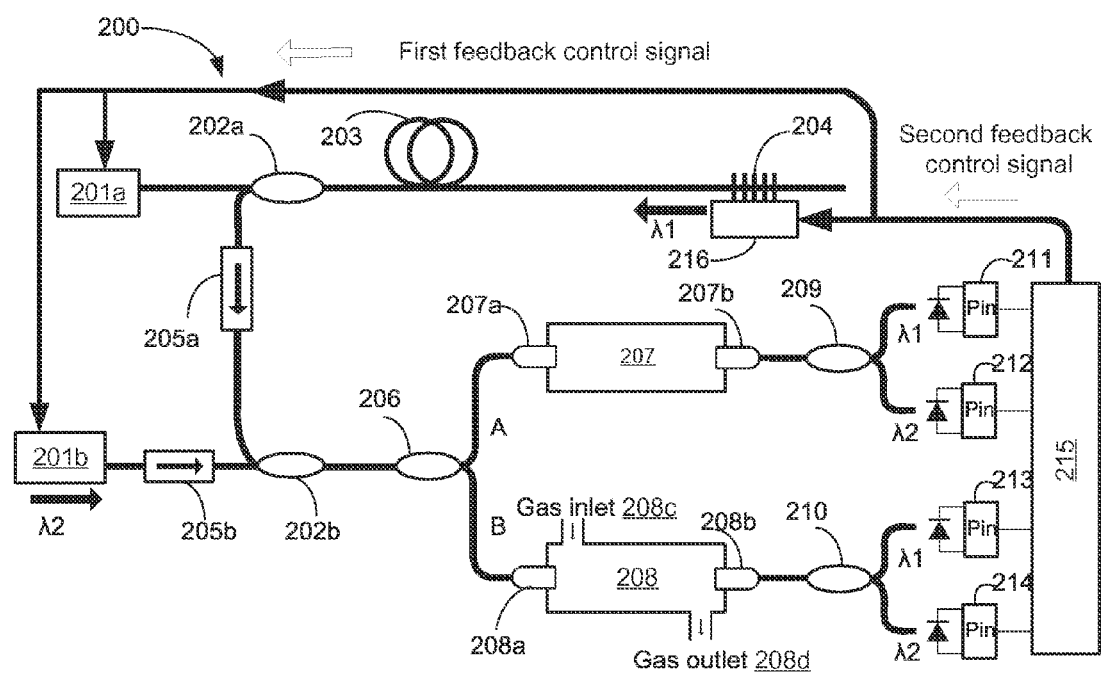
FIG. 2 schematically shows a gas detection system using a fiber laser of a double wavelength combination using reference-cavity compensation according to another embodiment of the present invention.

FIG. 2 shows another gas detection system of fiber laser with a double wavelength combination using reference cavity compensation according to another embodiment of the present invention. In the gas detection system 200 as shown in FIG. 2 according to the present invention, different from the embodiment shown in FIG. 1, the second fiber Bragg grating 104b in FIG. 1 is replaced by a laser 201b to provide as a second beam with the second wavelength $\lambda_2$ as the reference beam. The gas detection system 200 according to another embodiment of the present invention comprises a DFB fiber laser consisting of a laser diode pump source 201a, a first wavelength a division multiplexer 202a, an active optical fiber 203 and a fiber bragg grating 204 connected successively; a first optical isolator 205a coupled with the first wavelength division multiplexer 202a; a laser 201b; a second optical isolator 205b coupled with the laser 201b; a second wavelength division multiplexer 202b connected with the first optical isolator 205a and the second optical isolator 205b; a coupler 206 connected with the second wavelength division multiplexer 202b, the coupler 206 is connected with a reference gas chamber 207 and a detecting gas chamber 208, and the other ends of the reference gas chamber 207 and the detecting gas chamber 208 are connected respectively with a third wavelength division multiplexer 209 and a fourth wavelength division multiplexer 210, the light outputted from the third wavelength division multiplexer 209 is inputted into a first photoelectric detector respectively 211 and a second photoelectric detector 212, the light outputted from the fourth wavelength division multiplexer 210 is inputted into a third photoelectric detector respectively 213 and a fourth photoelectric detector 214 respectively, so that the optical signals are converted into the electrical signals, which are used for detect respectively the intensities of the light signals after the light passes through each gas chamber. The output ends of the first, second, third, and fourth photoelectric detectors 211, 212, 213, 214 are connected with the feedback control unit 215, so as to implement feedback control to the pump sources 101 and the laser control unit 116 and obtain a detecting result of the gas concentration by comparison calculation The laser 201b is preferably a semiconductor laser, more preferably a distributed feedback (DFB) semiconductor laser.

The DFB fiber laser emits a first light beam of a first wavelength $\lambda_1$ as a detecting beam, the laser 201b emits a second light beam of a second wavelength $\lambda_2$ as a reference beam. The first wavelength $\lambda_1$ is different from the second wavelength $\lambda_2$. The first wavelength $\lambda_1$ of the detecting light beam is the same as the characteristics absorption lines of the gas to be detected, and the second wavelength $\lambda_2$ of the reference beam is near the absorption lines of the gas to be detected, but with a distance away from its absorption lines. According to an embodiment of the present invention, when the gas to be detected is the methane gas, its characteristic absorption lines is 1.3 μm, at this time, the first wavelength of the first beam is 1.3 μm, and the second wavelength of the second beam is 1.5 μm, with an interval of 0.2 μm away from the first wavelength.

The function of the second optical isolator 205b is similar as that of the first optical isolator 205a, to prevent a reverse optical transmission in the optical fiber from interfering the output light of the gas detection system 100. The operating wavelength and the isolation degree of the first optical isolator 205a and the second optical isolator 205b are chosen based on the first and the second emission wavelength. According to a preferable embodiment of the present invention, the operating wavelength of the second optical isolator 205b is 1550 nm, the isolation degree is 40 dB.

Preferably, the second wavelength division multiplexer 202b is a 1×2 wavelength division multiplexer, allowing two lights of different wavelengths transmit in the same optical fiber.

The selection of other components parameters of the gas detection system 200 is similar to the gas detection system 100 shown in FIG. 1, the same content will not be described in details.

Figure 3:
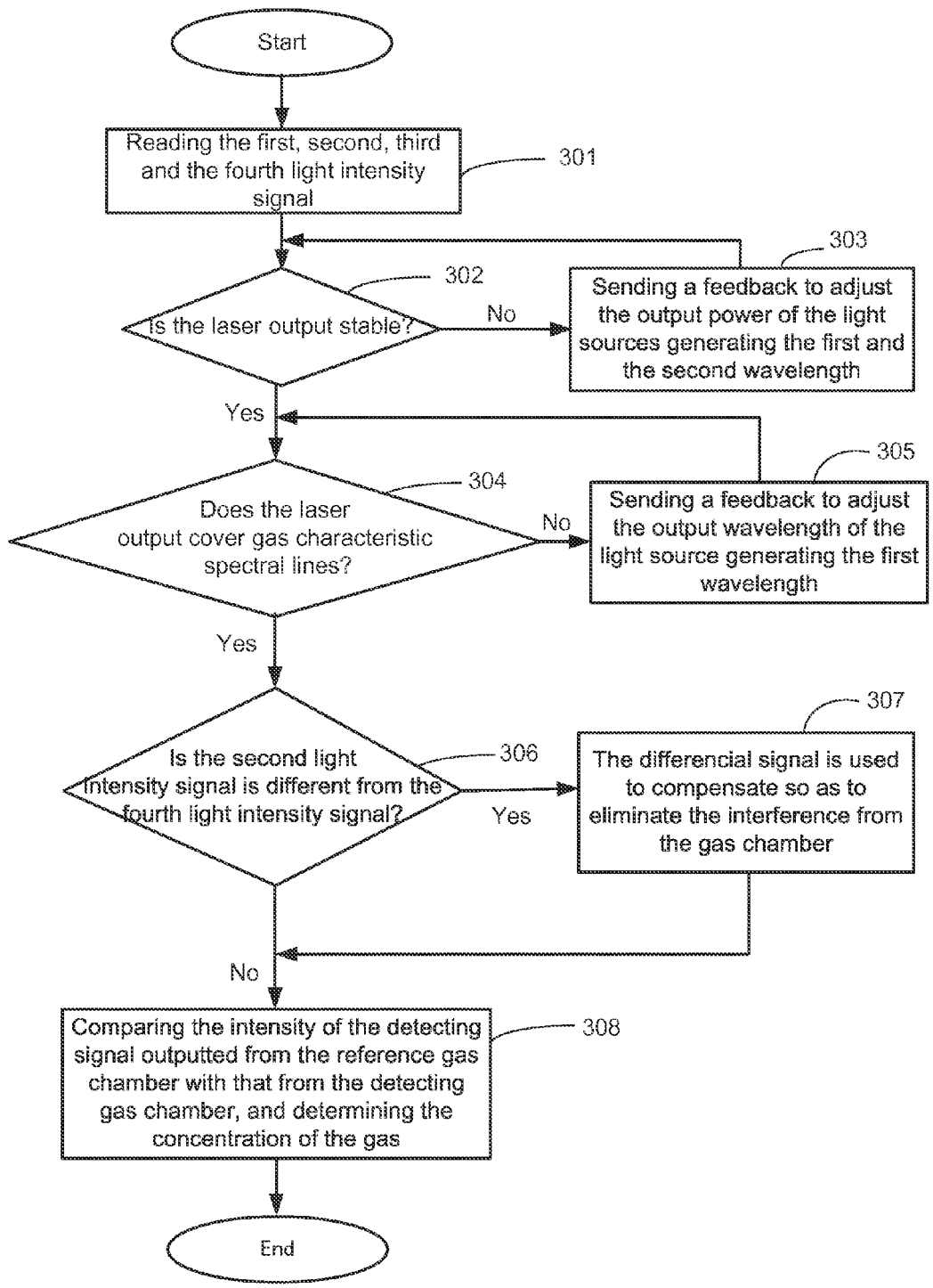
FIG. 3 schematically shows a flow chart of the feedback control method of the feedback control unit according to the present invention.

FIG. 3 shows a flow chart of the feedback control method of the feedback control unit according to the invention.

At step 301, the first light intensity signal outputted from the first photoelectric detector, the second light intensity signal outputted from the second photoelectric detector, the third light intensity signal outputted from the third photoelectric detector and the fourth light intensity signal outputted from the fourth photoelectric detector are read. The first light intensity signal indicates the light intensity signal after the laser beam of first wavelength $\lambda_1$ outputted from the optical fiber laser transmits through the reference gas chamber, as the detecting signal of the reference gas chamber, the second light intensity signal indicates the light intensity signal after the laser beam of second wavelength $\lambda_2$ outputted from the optical fiber laser transmits through the reference gas chamber, as the reference signal of the reference gas chamber. The third light intensity signal indicates the light intensity signal after the laser beam of first wavelength $\lambda_1$ outputted from the optical fiber laser transmits through the detecting gas chamber, as the detecting signal of the detecting gas chamber, the fourth light intensity signal indicates the light intensity signal after the laser beam of second wavelength $\lambda_2$ outputted from the optical fiber laser transmits through the detecting gas chamber, as the reference signal of the detecting gas chamber.

In order to obtain accurate measurement results, stable and accurate first, second, third and fourth light intensity signals are needed. Therefore, firstly, at step 302, it is determined whether the output of the light source emitting the first wavelength $\lambda_1$ and the second wavelength $\lambda_2$ is stable. In the embodiment shown in FIG. 1, the light sources emitting the first wavelength $\lambda_1$ and the second wavelength $\lambda_2$ are two DFB fiber lasers consisted of the first fiber Bragg grating 104a and the second fiber Bragg gratings 104b that output the different wavelengths of laser respectively; In the embodiment shown in FIG. 2, the light sources emitting the first wavelength $\lambda_1$ and the second wavelength $\lambda_2$ are a DFB fiber laser consisted of the fiber Bragg grating 104 and the laser 201b respectively. The stable laser signals generally are represented by signals having intensity in step form. When the system begins to operate, the light source usually is adjusted to a lower level of power output so as to protect the system. With the output power of the light sources increases and gradually reaches the operating threshold of the laser, a stable laser output is obtained. If at Step 302, it is determined that the laser output is not stable, then go to Step 303, the power outputs of the light sources emitting the first wavelength $\lambda_1$ and the second wavelength $\lambda_2$ is feedback adjusted by the first feedback control signal, for example the pump sources are feedback adjusted to gradually increase the output power of pump sources. Step 302 is repeated until the stability of the laser output is achieved, i.e., the output signals having intensity in step form as required in measurement are obtained.

Figure 4:
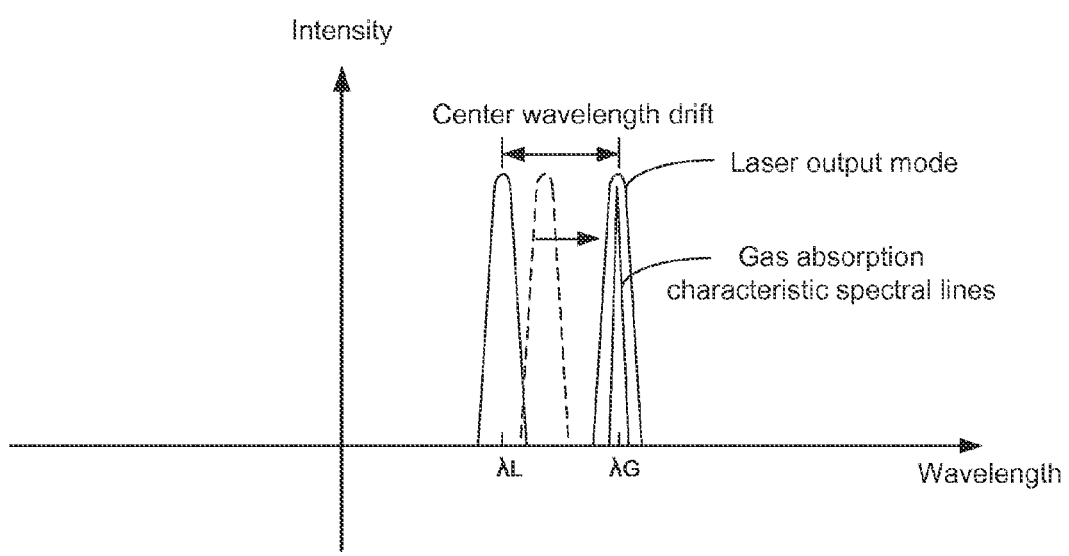
FIG. 4 schematically shows the feedback principle for feedback adjusting the drift of the beam wavelength outputted by the laser according to the present invention.

Then at Step 304, it is determined whether the wavelength range of the signal pattern outputted from the light source emitting the first wavelength $\lambda_1$ covers the characteristic spectral line of the gas to be detected. FIG. 4 shows the principle of feedback regulating the drift of the output wavelength of the laser beam according to the present invention. As shown in FIG. 4, the center wavelength of the absorption spectral lines of the gas to be detected is $\lambda_G$, the center wavelength of laser output mode is $\lambda_L$. If it is desired to measure the concentration of the gas to be detected by absorbing laser by gas, it is needed to adjust the output of laser so that the center wavelength outputted from the laser drifts until it completely covers the center wavelength of the absorption spectral line of the gas to be detected. Ideally, If $\lambda_G$ and $\lambda_L$ are substantially coincident with each other, the best effect of the measurement is achieved, that is to say, the output of the laser is completely absorbed by the reference gas and the gas to be detected, the intensity of the laser after passing through the reference gas chamber and the detecting gas chamber reduces significantly.

It can be determined whether the wavelength range of the signal model outputted from the light source emitting the first wavelength $\lambda_1$ covers the characteristic spectral line of the gas to be detected, by comparing the intensity of the first or third light intensity signal with that of the second or fourth light intensity signal emitted by the light source emitting the second wavelength $\lambda_2$ which is not absorbed by the gas. If the wavelength range of the signal model outputted from the light source emitting the first wavelength $\lambda_1$ is substantially coincident with the characteristic spectral line of the gas to be detected, the laser is absorbed completely, and the signal intensity of the first or the third light intensity signal will be significantly less than the second or the fourth light intensity signal not being absorbed by gas. If the wavelength misalignment leads to the light is not absorbed by gas, the signal intensity of the first or third light intensity signal should be substantially the same as that of the second or forth light intensity signal, and the attenuation of the first or third light intensity signal passing through the air chambers should be negligible. Comparing with the laser not absorbed by the gas, the attenuation degree of the intensity of the laser after being absorbed by the gas depends on the differences of the gas concentrations and absorption spectral lines of the gas to be detected.

If comparing the signal intensity values of the first or third signal intensity with that of the second or fourth signal intensity, it is found that the center wavelength of the output signal of the light source emitting the first wavelength $\lambda_1$ is not coincident with the center wavelength of the characteristics spectral line of the gas to be detected, go to Step 305, the feedback control unit transmits the second feedback control signal to the light source emitting the first wavelength $\lambda_1$ to change the output wavelength of the light source emitting the first wavelength, which control the beam wavelength of the laser output to drift till it move to be substantially coincident with the center wavelength of the characteristics absorption spectral lines of the gas to be detected. For example, in the embodiment shown in FIG. 1, when the laser control unit 116 is made of piezoelectric ceramic materials sheet or plate sheet, the laser control unit 116 deforms under the control of the feedback control signal, which makes the fiber Bragg grating 104a attached thereto deforms, thus changing the laser cavity length, changing the first wavelength $\lambda_1$ of the laser output which drifts until coincide with the center wavelength of the characteristics line of the gas. Then, go to step 306.

At step 306, it is determined whether there are differences between the signal intensity of the second light intensity signal (i.e., the reference wavelength signals of the reference gas chamber) outputted from the reference gas chamber and the signal intensity of the fourth light intensity signal (i.e., the reference wavelength signal of the detection gas chamber) outputted from the detecting gas chamber. If the signal intensity of the second light intensity signal and that of the fourth light intensity signals are determined to be the same, it indicates that the reference gas chamber and the detection gas chamber have the same measurement environment, then go to Step 308. If the two signal intensities are determined to be different, then go to Step 307 for wavelength correction, that is to say, the difference signals are used for compensation in order to eliminate the interference in the chamber caused by the environment differences between the reference gas chamber and the detection gas chamber to avoid the error results of the measurement. In the actual measurement, the wavelength drift may occur in the reference gas chamber and the detection gas chamber, due to the wavelength drift of the light source, the loss that the transmission path changes, the optical element drift in the air chamber etc. The differences between the second light intensity signal and the fourth light intensity signal can be used as a compensation amount to be added in the first and third light intensity signal for the subsequent comparative calculation, and then go to Step 308.

At Step 308, the signal intensities of the first light intensity signal (i.e., the detecting wavelength signals of the reference gas chamber) and the third light intensity signal (i.e., the detection wavelength signal of the detecting gas chamber) are compared, and the difference between the two intensity values indicates the comparing result of the concentrations of the gas to be detected and the reference gas. For example, if the intensity value of the third light intensity signal is greater than that of the first light intensity signal, the gas concentration of the detecting gas chamber 108 is greater than that in the reference gas chamber 107. Preferably, the comparison results can be outputted to an alarm device, which trigger the alarm signal when the alarm threshold is reached. According to the invention, because it is considered the differences of the third light intensity signal and the first light intensity signal are caused by the interference between the gas chambers, the measurement result of the concentration is more accurate, the gas concentration content of the trace concentration may be measured.

The gas detection system according to the present invention can be implemented to select different components parameters based on the type and the concentration of the gas to be detected. For example, the gas detection system of the present invention is applied to detect the methane content in an industrial environment. In the industrial environment, it is required that the content of methane gas is not higher than 4%, otherwise it will explode. When the gas detection system according to the present invention is used, the reference gas chamber is filled with the reference gas with a methane content of 4%, and the laser is adjusted to make the wavelength range of the laser output covers the center wavelength of the absorption characteristic spectral line of methane. Then, the gas detection system is placed in the environment to be detected, the inlet of the detecting gas chamber is open so that a certain amount of gas sample to be detected is introduced into the chamber, and then the gas inlet and gas outlet of the detecting gas chamber is closed. Next, the light sources emitting the first wavelength $\lambda_1$ and the second wavelength $\lambda_2$ of the gas detection system is open, so that laser outputted from the laser pass through the reference gas chamber and the detecting gas chamber respectively. The output of the laser is measured. Next, by adjusting the power of the light sources emitting the first wavelength $\lambda_1$ and the second wavelength $\lambda_2$ to be used and feedback adjusting the first wavelength, a stable laser output is achieved to cover the absorption spectrum line of methane gas. By comparing the light intensities of the laser passing through the reference gas chamber and the detecting gas chamber, it can be determined whether the concentration of the methane gas in this industrial environment exceeds the threshold value of methane content, and the alarm system is triggered immediately when it exceeds the threshold value.

The gas detection system according to the present invention can take advantages of the unique superiority of the compact structure and narrow linewidth of the laser output of the fiber laser, and achieve a gas detection method with high sensitive and high precision by feedback controlling. The method and system are not limited to apply to detection of gas content with high sensitivity, but also easily apply to the detection with high sensitivity and material analysis of other materials.

Combined with the disclosed description and practice of the present invention, it is easy for those skilled in the art to contemplate and understand other embodiments of the invention. The description and embodiments are merely exemplary, and the scope and spirit of the invention will be limited by the claims.

What is claimed is:
1. A fiber laser gas detection system with a double wavelength combination using reference cavity compensation, said system comprising
   an optical fiber laser emitting beams having first wavelength and second wavelength respectively, which consists of a laser diode pump source, a first wavelength division multiplexer, an active optical fiber, a first fiber bragg grating and a second fiber bragg grating connected successively, said first wavelength is different from said second wavelength, and said first wavelength is the same as the characteristic absorption spectral lines of the gas to be detected;
   an optical isolator coupling connected with said first wavelength division multiplexer, said optical isolator is used to prevent reverse light from transmitting in said active optical fiber;
   a coupler connected with said optical isolator for dividing the laser light after being synthesized by said first wavelength division multiplexer into a first and second outputs according to a certain power ratio;
   a reference gas chamber, which is filled with reference gas of the a known concentration and of the same composi- tion as that of the gas to be detected, and receives the first output beam from said coupler and make it pass through the reference gas;

a detection gas chamber, which is filled with the gas to be detected, and receives the second output beam from said coupler and make it pass through the gas to be detected;

a second wavelength division multiplexer connected with said reference gas chamber, for dividing the beam passing through the reference gas chamber into beams having said first wavelength and said second wavelength;

a third wavelength division multiplexer connected with said detecting gas chamber, for dividing the beam passing through the detecting gas chamber into beams having said first wavelength and said second wavelength;

a first photodetector connected to said second wavelength division multiplexer for receiving the divided beam having the first wavelength to generate a first light intensity signal;

a second photodetector connected to said second wavelength division multiplexer for receiving the divided beam having the second wavelength to generate a second light intensity signal;

a third photodetector connected to said third wavelength division multiplexer for receiving the divided beam having the first wavelength to generate a third light intensity signal;

a fourth photodetector connected to said third wavelength division multiplexer for receiving the divided beam having the second wavelength to generate a fourth light intensity signal; and a feedback control unit for receiving and comparing said first, second, third and fourth light intensity signals, and converting the comparison result into a feedback signal to adjust said pump source and said first fiber bragg grating.

2. The gas detection system as claimed in claim 1, wherein said coupler generates the first and second outputs according to the power ratio of 1:1.

3. The gas detection system as claimed in claim 1, wherein the feedback control method of the feedback control unit comprising the steps of:

a) determining whether the output of the fiber laser is stable, if it is not stable, sending a first feedback control signal to adjust the power output of the pump source until it is stable;

b) determining whether the wavelength range of the signal mode having the first wavelength covers the characteristics spectral lines of the gas to be detected, if it does not cover, sending a second feedback control signal to adjust the first fiber bragg grating until it covers;

c) determining whether the second light intensity signal is different from the fourth light intensity signal, if there is any difference, a signal indicating the difference is used for compensating the first light intensity signal and the third light intensity signal; and d) comparing the signal intensities of the first and third light intensity signals to obtain the result of comparing the concentrations of the gas to be detected and the reference gas.

4. The gas detection system as claimed in claim 3, wherein said determining in step b) is achieved by comparing if the signal intensity values of said first or third light intensity is substantially smaller than that of the second or the fourth light intensity signal.

5. The gas detection system as claimed in claim 3, further comprising a laser control unit attached to the first fiber bragg grating, and the deformation of the laser control unit is controlled by said second feedback control signal so as to change the laser resonator cavity length.

6. The gas detection system as claimed in claim 5, wherein the laser control unit is made of PZT piezoelectric ceramic or TE temperature control unit.

7. The gas detection system as claimed in claim 1, further comprising a spherical lens for respectively coupling said beams into the reference gas chamber and the detection gas chamber so as to emit therefrom.

8. The gas detection system as claimed in claim 1, wherein said second wavelength is near the absorption spectral line of the gas to be detected, but has a certain distance away from the said first wavelength.

9. The gas detection system as claimed in claim 1, wherein the active fiber is selected from any of an ytterbium-doped fiber, erbium-doped fiber or erbium ytterbium co-doped fiber.

10. A fiber laser gas detection system with a double wavelength combination using reference cavity compensation, said system comprising:

an optical fiber laser emitting a beam having a first wavelength, which consists of a laser diode pump source, a first wavelength division multiplexer, an active optical fiber and a fiber bragg grating connected successively, a laser light source emitting the beam having a second wavelength which is different from the first wavelength, said first wavelength is the same as the characteristic absorption spectral lines of the gas to be detected;

a first optical isolator coupling connected with said first wavelength division multiplexer, said first optical isolator is used to prevent reverse light from transmitting in said active optical fiber;

a second optical isolator coupling connected with said laser light source, said second optical isolator is used to prevent reverse light from transmitting in said active optical fiber;

a second wavelength division multiplexer connected with said first and second optical fiber, for synthesizing the beams having the first and the second wavelength into one beam to output;

a coupler connected with said second wavelength division multiplexer for dividing the laser light after being synthesized by said second wavelength division multiplexer into a first and second outputs according a certain power ratio;

a reference gas chamber, which is filled with the reference gas of a known concentration and of the same composition as that of the gas to be detected, and receives the first output beam from said coupler and make it pass through the reference gas;

a detection gas chamber, which is filled with the gas to be detected, and receives the second output beam from said coupler and make it pass through the gas to be detected;

a third wavelength division multiplexer connected with said reference gas chamber, for dividing the beam passing through the reference gas chamber according to said first wavelength and said second wavelength;

a fourth wavelength division multiplexer connected with said detecting gas chamber, for dividing the beam passing through the detecting gas chamber according to said first wavelength and said second wavelength;

a first photodetector connected to said third wavelength division multiplexer, for receiving the divided beam having the first wavelength to generate a first light intensity signal;

a second photodetector connected to said third wavelength division multiplexer, for receiving the divided beam having the second wavelength to generate a second light intensity signal;

a third photodetector connected to said fourth wavelength division multiplexer, for receiving the divided beam having the first wavelength to generate a third light intensity signal;

a fourth photodetector connected to said fourth wavelength division multiplexer, for receiving the divided beam having the second wavelength to generate a fourth light intensity signal;

a feedback control unit for receiving and comparing said first, second, third and fourth light intensity signals, and converting the comparison result into a feedback signal to adjust said pump source, said fiber bragg grating and said laser light source.

* * * * *